United States Patent [19]

Bodor et al.

[11] 4,061,753

[45] Dec. 6, 1977

[54] TREATING PSORIASIS WITH TRANSIENT PRO-DRUG FORMS OF XANTHINE DERIVATIVES

[75] Inventors: Nicolae S. Bodor, Lawrence; Kenneth B. Sloan, Eudora, both of Kans.

[73] Assignee: INTERx Research Corporation, Lawrence, Kans.

[21] Appl. No.: 655,786

[22] Filed: Feb. 6, 1976

[51] Int. Cl.$^2$ .............................................. A61K 31/52
[52] U.S. Cl. .................................. 424/253; 260/254; 260/256; 542/427
[58] Field of Search ........................ 260/256; 424/253

[56] References Cited

FOREIGN PATENT DOCUMENTS 1,265,879  5/1961  France ................................ 260/256
1,226,587  10/1966  Germany ........................... 260/256

OTHER PUBLICATIONS

Roth et al., Chemical Abstracts, 64:5093g.
Burckhalter et al., J. Org. Chem., 24, pp. 562–564 (1959).

*Primary Examiner*—Paul M. Coughlan, Jr.
*Attorney, Agent, or Firm*—Charles N. Blitzer

[57] ABSTRACT

Compounds of the formula:

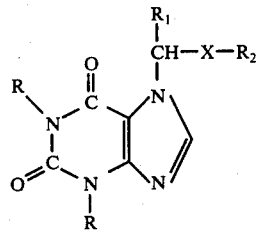

wherein R, which may be the same or different, represents a member selected from the group consisting of —CH$_3$, —C$_2$H$_5$, —C$_3$H$_7$, iso—C$_3$H$_7$, —C$_4$H$_9$, iso—C$_4$H$_9$, pentyl, benzyl, allyl, 2-hydroxyethyl, cyclohexyl, 2-isobutenyl, hydroxymethyl, 2-phenylethyl and -CH$_2$O-R$_2$, wherein R$_2$ is defined infra; wherein R$_1$ represents a member selected from the group consisting of H, C$_1$–C$_7$ straight or branched alkyl, CCl$_3$, CBr$_3$, CI$_3$,

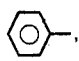

CH$_3$O—CH$_2$—, (CH$_3$)$_2$NCH$_2$—,

—CHO, <phenyl>—O—CH$_2$—, <phenyl>—CH=CH—,

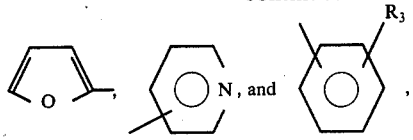

wherein R$_3$ represents a member selected from the group consisting of -OH, halogen (Cl, Br, I), —OCH$_3$, -COOCH$_3$, -NO$_2$ and -OCOCH$_3$; wherein

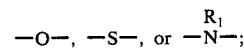

and wherein R$_2$ represents a member selected from the group consisting of

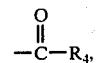

wherein R$_4$ is a member selected from the group consisting of C$_2$–C$_{20}$ straight or branched alkyl (C$_3$–C$_7$ preferred), —[—(CH$_2$)$_m$—], wherein *m* represents an integer of from 0 to 10,

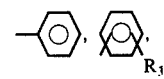

wherein R$_3$ is defined as above,

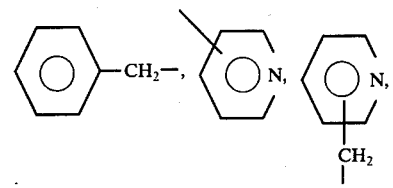

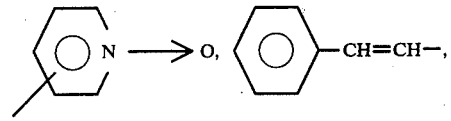

the residue of any naturally occurring amino acid, the residue of any N- substituted amino acid, wherein said substituent is any amino acid protective group cleavable via hydrogenolysis or hydrolysis (e.g., formyl, benzyloxy, carbonyl, t-butyloxycarbonyl), the residue of an N,N-C$_1$-C$_5$-dialkyl or cycloalkylamino acid,

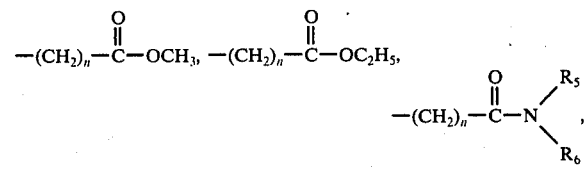

wherein *n* represents an integer of from 1–5 and R$_5$ and $R_6$ which may be the same or different represent $C_1$–$C_5$ alkyl or together form a heterocyclic ring with the N atom to which they are attached (e.g., pyrolidine, piperidine, morpholine, piperazine, imidazoline, thiazolidine, isoxazolidine), imidazolyl, O-$C_1$–$C_8$ alkyl, O-benzyl, O-phenyl and

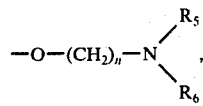

wherein $n$, $R_5$ and $R_6$ are defined as above; and wherein $R^2$ further represents a member selected from the group consisting of straight or branched $C_1$–$C_{20}$ alkyl,

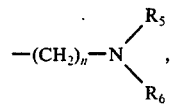

wherein $n$, $R_5$ and $R_6$ are defined as above, phenyl, tolyl, xylyl, and —$SO_2$—$R_7$, wherein $R_7$ is a straight or branched $C_1$–$C_{20}$ alkyl useful in treating psoriasis in warm-blooded animals are provided.

99 Claims, No Drawings

TREATING PSORIASIS WITH TRANSIENT PRO-DRUG FORMS OF XANTHINE DERIVATIVES

BACKGROUND OF THE INVENTION

1. Field of the Invention

The present invention is directed to novel transient pro-drug forms of certain xanthine derivatives useful in (1) elevating intracellular cyclic AMP* levels, and (2) the treatment of psoriasis in warm-blooded animals.
*Adenosine monophosphate For the purposes of this application, the term "pro-drug" denotes a derivative of a known and proven prior art xanthine compound (e.g., theophylline), which derivative, when administered topically to a warm-blooded animal, "cleaves" in such a manner as to release the proven drug form in the dermal tissue thereof.

The term "transient" denotes dermal enzymatic and/or chemical hydrolytic "cleavage" of the compounds of the instant invention in such a manner that the proven drug form (parent xanthine compound, e.g., theophylline) is released and the remaining "cleaved" moiety remains nontoxic and metabolized in such a manner that nontoxic, metabolic products are produced.

2. Description of the Prior Art

The development of pro-drug forms of certain xanthine compounds such as theophylline was initiated in order that such compounds could be used in the treatment of psoriasis. The rational use of theophylline and other chemically related xanthine compounds to treat psoriasis is based on three documented observations:

a. that psoriatic conditions stem from increased cell division of the skin which in many ways mimics cancerous cell division, J. J. Voorhees, E. A. Duell, M. Stawiski and E. K. Harrell, Clin. *Pharmacol. Therap.*, 16, 919 (1974);

b. that theophylline and similarly related xanthine compounds decrease the degradation of cyclic AMP by inhibiting phosphodiesterase activity, E. W. Sutherland and T. W. Rall, *J. Biol. Chem.*, 232, 1077 (1958); and c. that cyclic AMP can inhibit malignant cell growth in culture, G. S. Johnson, R. M. Friedman, I. Pastan, Proc. Natl. *Acad. Sci. U.S.A.*, 68, 425 (1971) and A. N. Hsie and T. T. Puck, Ibid., p. 1316, respectively.

A direct correlation between percutaneous absorption and partition coefficients of the absorbed compound in water and some lipid-like materials, e.g., oil, heptane octanol has been shown. See, M. Katz and Z. I. Shaiki, *J. Pharm. Sci.*, 54, 591 (1965) and J. E. Treherne, *J. Physiol.*, 133, 171 (1956). The closer this partition coefficient is to unity, the better the compound is absorbed, providing, however, the compound in question has appreciable solubility in both the water and lipid phase. However, if anything, the skin is more permeable to lipid soluble substances. See, J. H. Wills, "Percutaneous Absorption" in *Pharmacology and The Skin*, W. Montagny, E. J. Van Scott and R. B. Stoughton, Ed., Chapter XII, Appleton-Century Grofts, New York, New York, 1972, p. 172. Certain Xanthine compounds, such as theophylline, on the other hand, are almost insoluble in lipid-like solvents (e.g., heptane). Consequently, their use in the treatment of psoriasis has heretofore been limited. Moreover, the above also makes it very clear that the target pro-drug of the xanthine compound employed should have an increased lipid solubility and a partition coefficient near unity if it is to be absorbed percutaneously and reach the site where therapeusis is required.

The remaining criteria for the target pro-drug is that it undergo rapid hydrolysis once it reaches its site of therapeutic activity. One candidate which appears to meet the above criteria is the 7-acyloxymethyl derivative of theophylline. Acyloxymethyl esters of ampicillin have been shown to be readily hydrolyzed by esterases and other enzymes present in serum and tissue homogenates of man. See, W. V. Daehne, et al., *J. Med. Chem.*, 13, 607 (1970). In the case of theophylline, hydrolysis would initially lead to the 7-hydroxymethyl derivative which the present inventors have found to be extremely unstable in water. Accordingly, it would generate theophylline in vivo. It has also been found that incorporation of a long chain aliphatic acid into theophylline or the remaining parent xanthine compounds of the instant invention increases the lipid solubility of the same.

SUMMARY OF THE INVENTION

It is one object of the present invention to provide novel, transient pro-drug forms of selected xanthine compounds (e.g., theophylline), which are extremely useful in the treatment of psoriasis in warm-blooded animals, e.g., humans, raising cyclic AMP levels by inhibition of phosphodiesterase activity.

It is another object of the present invention to provide novel, transient pro-drug forms of selected xanthine derivatives which following topical administration to the skin of a warm-blooded animal will cleave in such a manner as to enable the original parent xanthine moiety (e.g., theophylline) to be released at its therapeutic site of anti-psoriatic activity and to further permit the cleaved moiety(ies) unassociated with the parent xanthine moiety to be metabolized in a nontoxic fashion.

The foregoing objects are achieved by topically administering to a warm-blooded animal afflicted with psoriasis an effective antipsoriatic amount of a compound having the formula:

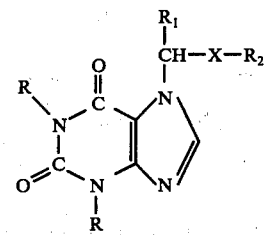

wherein R, which may be the same or different, represents a member selected from the group consisting of —CH$_3$, —C$_2$H$_5$, —C$_3$H$_7$, iso—C$_3$H$_7$, —C$_4$H$_9$, iso—C$_4$H$_9$, pentyl, benzyl, allyl, 2-hydroxyethyl, cyclohexyl, 2-isobutenyl, hydroxymethyl, 2-phenylethyl and —CH$_2$O—R$_2$, wherein R$_2$ is defined infra; wherein R$_1$ represents a member selected from the group consisting of H, C$_1$–C$_7$ straight or branched alkyl, CCl$_3$, CBr$_3$, CI$_3$,

CH$_3$O—CH$_2$—, (CH$_3$)$_2$NCH$_2$—,

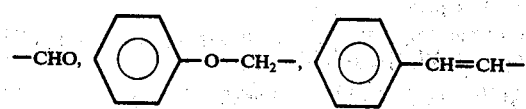

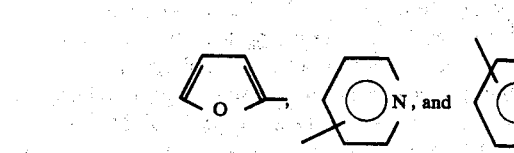

wherein R₃ represents a member selected from the group consisting of —OH, halogen (Cl, Br, I), —OCH₃, —COOCH₃, —NO₂ and —OCOCH₃; wherein X is

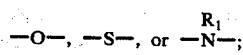

and wherein R₂ represents a member selected from the group consisting of

wherein R₄ is a member selected from the group consisting of $C_2$–$C_{20}$ straight or branched alkyl ($C_3$–$C_7$ preferred), —[—(CH₂)ₘ—], wherein m represents an integer of from 0 to 10,

wherein R₃ is defined as above

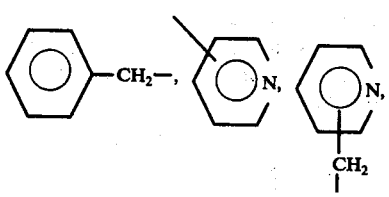

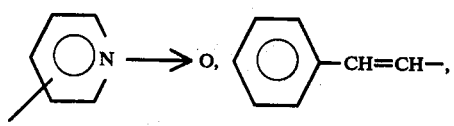

the residue of any naturally occurring amino acid, the residue of any N—substituted amino acid, wherein said substituent is any amino acid protective group cleavable via hydrogenolysis or hydrolysis (e.g., formyl, benzyloxy, carbonyl, t-butyloxycarbonyl), the residue of an N,N,—C₁—C₅—dialkyl or cycloalkylamino acid,

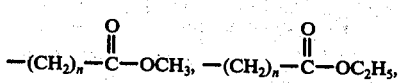

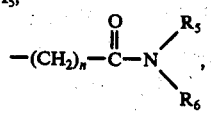

wherein n represents an integer of from 1–5 and R₅ and R₆ which may be the same or different represent $C_1$–$C_5$ alkyl or together form a heterocyclic ring with the N atom to which they are attached (e.g., pyrolidine, piperidine, morpholine, piperazine, imidazoline, thiazolidine, isoxazolidine), imidazolyl, O—$C_1$–$C_8$ alkyl, O-benzyl, O-phenyl and

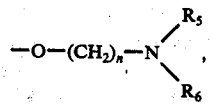

wherein n, R₅ and R₆ are defined as above; and wherein R₂ further represents a member selected from the group consisting of straight or branched $C_1$–$C_{20}$ alkyl,

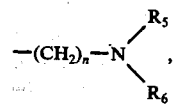

wherein n, R₅ and R₆ are defined as above, phenyl, tolyl, xylyl, and —SO₂—R₇, wherein R₇ is a straight or branched $C_1$–$C_{20}$ alkyl useful in treating psoriasis in warm-blooded animals are provided.

As used herein, the term "naturally occurring amino acid" includes without limitation:

| Glycine | Arginine |
|---|---|
| Alanine | Lysine |
| Valine | Hydroxylsine |
| Leucine | Phenylalanine |
| Isoleucine | Tyrosine |
| Cysteine | Asparagine |
| Cystine | Glutamine |
| Methionine | Proline |
| Serine | Hydroxyproline |
| Threonine | Histidine |
| Aspartic acid | Tryptophan |
| Glutamic acid | Pyroglutamic acid |

Similarly, the import of the phrase "amino acid protective group 'cleavable' via hydrogenolysis or hydrolysis" can be further gained from a review of U.S. Pat. No. 3,803,120 - Felix.

DETAILED DESCRIPTION OF THE INVENTION

While all the compounds encompassed within the above-described generic formula satisfy the objectives of the instant invention, nevertheless, certain selected compounds, as set out below, remain preferred:

1. 7-Ethoxymethyl-theophylline
2. 7-Propyloxymethyl-theophylline
3. 7-Butyloxymethyl-theophylline
4. 7-Benzyloxymethyl-theophylline
5. 7-(1-Pyridyl)methyl-theophylline chloride
6. 7-(N,N-dimethylaminoethyloxy)methyl-theophylline
7. 7-Acetyloxymethyl-theophylline
8. 7-Propionyloxymethyl-theophylline
9. 7-Butanoyloxymethyl-theophylline
10. 7-Pivalyloxymethyl-theophylline
11. 7-Hexanoyloxymethyl-theophylline
12. 7-Heptanoyloxymethyl-theophylline
13. 7-Octanoyloxymethyl-theophylline
14. 7-Ethoxycarbonyloxymethyl-theophylline
15. 7-Benzyloxycarbonyloxymethyl-theophylline
16. 7-(2',2',2'-Trichloroethyloxycarbonyloxymethyl)-theophylline
17. 7-(N,N-Dimethylglycyloxymethyl)-theophylline
18. 7-(1-Piperidylacetyloxymethyl)-theophylline 19. 7-Benzoyloxymethyl-theophylline
20. 7-p-Toluyloxymethyl-theophylline
21. 7-Phenylacetyloxymethyl-theophylline
22. 7-Picolinoyloxymethyl-theophylline
23. 7-Nicotinoyloxymethyl-theophylline
24. 7-N-Formylglycyloxymethyl-theophylline
25. 7-Glycyloxymethyl-theophylline
26. 7-Cinnamoyloxymethyl-theophylline
27. 7-N-Benzyloxycarbonylglycyloxymethyl-theophylline
28. 7-Methylsuccinyloxymethyl-theophylline
29. 7-(N,N-Dimethylsuccinamyloxymethyl)-theophylline
30. 7-(N,N-Diethylsuccinamyloxymethyl)-theophylline
31. 7-(N,N,N-Trimethylglycyloxymethyl)-theophylline chloride
32. 7-(N,N,N-Triethylglycyloxymethyl)-theophylline chloride
33. 7-(α-Ethoxyethyl)-theophylline
34. 7-(α-Benzyloxyethyl)-theophylline
35. 7-(α-Acetyloxyethyl)-theophylline
36. 7-(α-Propionyloxyethyl)-theophylline
37. 7-(α-Butanoyloxyethyl)-theophylline
38. 7-(α-Pivalyloxyethyl)-theophylline
39. 7-(α-Hexanoyloxyethyl)-theophylline
40. 7-(α-Octanoyloxyethyl)-theophylline
41. 7-(α-Ethoxycarbonyloxyethyl)-theophylline
42. 7-[α-(N,N-Dimethylglycyloxy)ethyl]-theophylline
43. 7-[α-(1-Piperidylacetyloxy)ethyl]-theophylline
44. 7-(α-Benzoyloxyethyl)-theophylline
45. 7-(α-Picolinoyloxyethyl)-theophylline
46. 7-[α-(N-Formylglycyloxy)ethyl]-theophylline
47. 7-[α-(N-Benzyloxycarbonylglycyloxy)ethyl]-theophylline
48. 7-(α-Methylsuccinyloxyethyl)-theophylline
49. 7-[α-(N,N-Dimethylsuccinamyloxy)ethyl]-theophylline
50. 7-[α-(N,N,N-Trimethylglycyloxy)ethyl]-theophylline chloride
51. 7-(α-Ethoxybenzyl)-theophylline
52. 7-(α-Benzyloxybenzyl)-theophylline
53. 7-(α-Acetyloxybenzyl)-theophylline
54. 7-(α-Propionyloxybenzyl)-theophylline
55. 7-(α-Butanoyloxybenzyl)-theophylline
56. 7-(α-Pivalyloxybenzyl)-theophylline
57. 7-(α-Hexanoyloxybenzyl)-theophylline
58. 7-(α-Octanoyloxybenzyl)-theophylline
59. 7-(α-Ethoxycarbonyloxybenzyl)-theophylline
60. 7-[α-(N,N-Dimethylglycyloxy)benzyl]-theophylline
61. 7-[α-(1-Piperidylacetyloxy)benzyl]-theophylline
62. 7-(α-Benzoyloxybenzyl)-theophylline
63. 7-(α-Picolinoyloxybenzyl)-theophylline
64. 7-[α-(N-Formylglycyloxy)benzyl]-theophylline
65. 7-[α-(N-Benzyloxycarbonylglycyloxy)benzyl]-theophylline
66. 7-(α-Methylsuccinyloxybenzyl)-theophylline
67. 7-[α-(N,N-Dimethylsuccinamyloxy)benzyl]-theophylline
68. 7-[α-(N,N,N-Trimethylglycyloxy)benzyl]-theophylline chloride
69. 7-Ethoxymethyl-1-methyl-3-isobutylxanthine
70. 7-Propyloxymethyl-1-methyl-3-isobutylxanthine
71. 7-Butyloxymethyl-1-methyl-3-isobutylxanthine
72. 7-Benzyloxymethyl-1-methyl-3-isobutylxanthine
73. 7-(1-Pyridyl)methyl-1-methyl-3-isobutylxanthine chloride
74. 7-(N,N-dimethylaminoethyloxy)methyl-1-methyl-3-isobutylxanthine
75. 7-Acetyloxymethyl-1-methyl-3-isobutylxanthine
76. 7-Propionyloxymethyl-1-methyl-3-isobutylxanthine
77. 7-Butanoyloxymethyl-1-methyl-3-isobutylxanthine
78. 7-Pivalyloxymethyl-1-methyl-3-isobutylxanthine
79. 7-Hexanoyloxymethyl-1-methyl-3-isobutylxanthine
80. 7-Heptanoyloxymethyl-1-methyl-3-isobutylxanthine
81. 7-Octanoyloxymethyl-1-3-isobutylxanthine
82. 7-Ethoxycarbonyloxymethyl-1-methyl-3-isobutylxanthine
83. 7-Benzyloxycarbonyloxymethyl-1-methyl-3-isobutylxanthine
84. 7-(2′,2′,2′-Trichloroethyloxycarbonyloxymethyl)-1-methyl-3-isobutylxanthine
85. 7-(N,N-Dimethylglycyloxymethyl)-1-methyl-3-isobutylxanthine
86. 7-(1-Piperidylacetyloxymethyl)-1-methyl-3-isobutylxanthine
87. 7-Benzoyloxymethyl-1-methyl-3-isobutylxanthine
88. 7-p-Toluyloxymethyl-1-methyl-3-isobutylxanthine
89. 7-Phenylacetyloxymethyl-1-methyl-3-isobutylxanthine
90. 7-Picolinoyloxymethyl-1-methyl-3-isobutylxanthine
91. 7-Nicotinoyloxymethyl-1-methyl-3-isobutylxanthine
92. 7-N-Formylglycyloxymethyl-1-methyl-3-isobutylxanthine
93. 7-Glycyloxymethyl-1-methyl-3-isobutylxanthine
94. 7-Cinnamoyloxymethyl-1-methyl-3-isobutylxanthine
95. 7-N-Benzyloxycarbonylglycyloxymethyl-1-methyl-3-isobutylxanthine
96. 7-Methylsuccinyloxymethyl-1-methyl-3-isobutylxanthine
97. 7-(N,N-Dimethylsuccinamyloxymethyl)-1-methyl-3-isobutylxanthine
98. 7-(N,N-Diethylsuccinamyloxymethyl)-1-methyl-3-isobutylxanthine
99. 7-(N,N,N-Trimethylglycyloxymethyl)-1-methyl-3-isobutylxanthine chloride
100. 7-(N,N,N-Triethylglycyloxymethyl)-1-methyl-3-isobutylxanthine chloride
101. 7-(α-Ethoxyethyl)-1-methyl-3-isobutylxanthine
102. 7-(α-Benzyloxyethyl)-1-methyl-3-isobutylxanthine
103. 7-(α-Acetyloxyethyl)-1-methyl-3-isobutylxanthine
104. 7-(α-Propionyloxyethyl)-1-methyl-3-isobutylxanthine
105. 7-(α-Butanoyloxyethyl)-1-methyl-3-isobutylxanthine
106. 7-(α-Pivalyloxyethyl)-1-methyl-3-isobutylxanthine
107. 7-(α-Hexanoyloxyethyl)-1-methyl-3-isobutylxanthine
108. 7-(α-Octanoyloxyethyl)-1-methyl-3-isobutylxanthine
109. 7-(α-Ethoxycarbonyloxyethyl)-1-methyl-3-isobutylxanthine 110. 7-[α-(N,N-Dimethylglycyloxy)ethyl]-1-methyl-3-isobutylxanthine
111. 7-[α-(1-Piperidylacetyloxy)ethyl]-1-methyl-3-isobutylxanthine
112. 7-(α-Benzoyloxyethyl)-1-methyl-3-isobutylxanthine
113. 7-(α-Picolinoyloxyethyl)-1-methyl-3-isobutylxanthine
114. 7-[α-(N-Formylglycyloxy)ethyl]-1-methyl-3-isobutylxanthine
115. 7-[α-(N-Benzyloxycarbonylglycyloxy)ethyl]-1-methyl-3-isobutylxanthine
116. 7-(α-Methylsuccinyloxyethyl)-1-methyl-3-isobutylxanthine
117. 7-[α-(N,N-Dimethylsuccinamyloxy)ethyl]-1-methyl-3-isobutylxanthine
118. 7-[α-(N,N,N-Trimethylglycyloxy)ethyl]-1-methyl-3-isobutylxanthine chloride
119. 7-(α-Ethoxybenzyl)-1-methyl-3-isobutylxanthine
120. 7-(α-Benzyloxybenzyl)-1-methyl-3-isobutylxanthine
121. 7-(α-Acetyloxybenzyl)-1-methyl-3-isobutylxanthine
122. 7-(α-Propionyloxybenzyl)-1-methyl-3-isobutylxanthine
123. 7-(α-Butanoyloxybenzyl)-1-methyl-3-isobutylxanthine
124. 7-(α-Pivalyloxybenzyl)-1-methyl-3-isobutylxanthine
125. 7-(α-Hexanoyloxybenzyl)-1-methyl-3-isobutylxanthine
126. 7-(α-Octanoyloxybenzyl)-1-methyl-3-isobutylxanthine
127. 7-(α-Ethoxycarbonyloxybenzyl)-1-methyl-3-isobutylxanthine
128. 7-[α-(N,N-Dimethylglycyloxy)benzyl]-1-methyl-3-isobutylxanthine
129. 7-[α-(1-Piperidylacetyloxy)benzyl]-1-methyl-3-isobutylxanthine
130. 7-(α-Benzoyloxybenzyl)-1-methyl-3-isobutylxanthine
131. 7-(α-Picolinoyloxybenzyl)-1-methyl-3-isobutylxanthine
132. 7-[α-(N-Formylglycyloxy)benzyl]-1-methyl-3-isobutylxanthine
133. 7-[α-(N-Benzyloxycarbonylglycyloxy)benzyl]-1-methyl-3-isobutylxanthine
134. 7-(α-Methylsuccinyloxybenzyl)-1-methyl-3-isobutylxanthine
135. 7-[α-(N,N-Dimethylsuccinamyloxy)benzyl]-1-methyl-3-isobutylxanthine
136. 7-[α-(N,N,N-Trimethylglycyloxy)benzyl]-1-methyl-3-isobutylxanthine chloride
137. 7-Acetylthiomethyl-theophylline
138. 7-Propionylthiomethyl-theophylline
139. 7-Butanoylthiomethyl-theophylline
140. 7-Pivalylthiomethyl-theophylline
141. 7-Hexanoylthiomethyl-theophylline
142. 7-Heptanoylthiomethyl-theophylline
143. 7-Octanoylthiomethyl-theophylline
144. 7-(N,N-Dimethylglycylthiomethyl)-theophylline
145. 7(1-Piperidylacetylthiomethyl)-theophylline
146. 7-Benzoylthiomethyl-theophylline
147. 7-p-Toluylthiomethyl-theophylline
148. 7-Phenylacetylthiomethyl-theophylline
149. 7-Picolinoylthiomethyl-theophylline
150. 7-Nicotinoylthiomethyl-theophylline
151. 7-N-Formylglycylthiomethyl-theophylline
152. 7-Glycylthiomethyl-theophylline
153. 7-Cinnamoylthiomethyl-theophylline
154. 7-(N,N-Diethylsuccinamylthiomethyl)-theophylline
155. 7-(N,N,N-Trimethylglycylthiomethyl)-theophylline chloride
156. 7-(N,N,N-Triethylglycylthiomethyl)-theophylline chloride
157. 7-(N,N-Diethylaminomethyl)-theophylline
158. 7-(N-Methylacetamidomethyl)-theophylline
159. 7-(N,N-Diethylglycylamidomethyl)-theophylline
160. 7-(N,N-Diethylamidosuccinamylamidomethyl)-theophylline From among the foregoing compounds, certain selected compounds are preferred and are claimed herein.

The compounds of the instant invention are easily prepared in accordance with those step-wise procedures outlined below.

The majority of those compounds encompassed within the above-described generic formula are prepared using two basic approaches. For convenience, theophylline will be employed as a mode xanthine compound in the reaction schemes which follow:

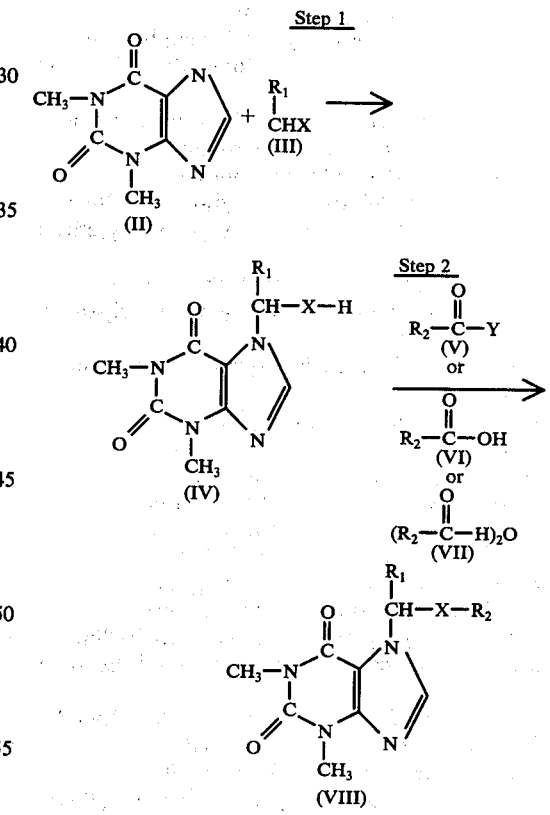

(1) $R_1$ and $R_2$ are defined as above.
(2) X is defined as above.
(3) Y is Cl, Br or I.

Step (1) is carried out in aqueous solution, using an excess of the aldehyde. The reaction is carried out at a temperature of from 0° C to 100° C, at standard pressure, over a period of time ranging from one to 24 hours and further, in the presence of a basic catalyst such as trimethylamine, triethylamine, N-methylmorpholine, etc.

Alternatively, the same reaction can be carried out in the presence of a suitable organic solvent such as benzene, dimethylformamide, chloroform, etc., between room temperature and the boiling point of the solvent employed, standard pressure, and over a period of time ranging from one to 24 hours, employing a basic catalyst as described above, or an acid catalyst such as p-toluenesulfonic acid, $ZnCl_2$, sulfosalicylic acid, etc. In this procedure, an excess of aldehyde is required. As a second alternative, the same reaction can be carried out in the absence of a solvent or an excess of aldehyde when the aldehyde is employed as a solvent, per se. The reaction conditions employed are synonymous with those employed in the first alternative procedure described above. In addition, in this alternative procedure, the need for a basic or acid catalyst is optional.

The compound of formula IV obtained from step (1) can be isolated via standard crystallization procedures, and if need be, the compound can be recrystallized from any suitable anhydrous organic solvent such as benzene, tetrahydrofuran, acetone, chloroform, etc.

In step (2), acylation is carried out conventionally. For instance, one may react the product obtained from step (1) with a compound designated as $$R_2-\overset{O}{\underset{\|}{C}}-Y,$$

wherein Y is defined as above, in the presence of any suitable organic halocarbon solvent such as chloroform, dichloromethane, etc. and an acid scavenger such as trimethylamine, triethylamine, N-methylmorpholine, etc. The reaction is carried out at standard pressure, over a temperature range of from 0° C to the boiling point of the solvent employed and for a period of time ranging from one to 24 hours.

In an alternative procedure, the product of step (1) can be reacted with a compound designated as $$R_2-\overset{O}{\underset{\|}{C}}-OH$$

in the presence of an organic halocarbon solvent as described above, e.g., tetrahydrofuran, dioxane, etc. and a dehydrating agent such as dicyclohexylcarbodiimide (DCCI), 2-ethoxycarbonylethoxydihydroquinidine (EEDQ). This reaction is carried out at room temperature, standard pressure, and over a period of time ranging from one to 24 hours.

Finally, and yet another alternative procedure, the product of step (1) can be reacted with a compound designated as $$(R_2-\overset{O}{\underset{\|}{C}}-H)_2O$$

in the presence of any organic solvent noted above and in the further presence of an organic base such as trimethylamine, triethylamine, pyridine, etc. The reaction conditions employed are those of standard pressure and room temperature with a reaction time of one to 24 hours.

The compound of formula (VIII) can be obtained via standard crystallization procedures, and if necessary, recrystallization can be carried out in the presence of a suitable anhydrous organic solvent as illustrated earlier.

The second procedure for preparing the majority of those compounds encompassed by the above-described generic formula is illustrated below:

REACTION "A"

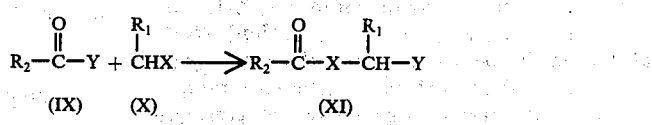

REACTION "B"

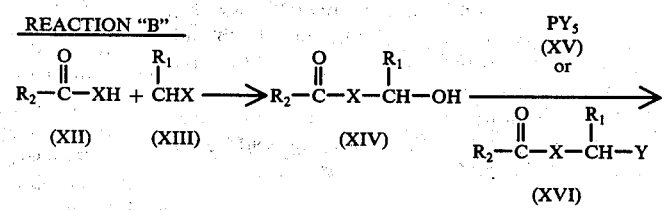

REACTION "C"

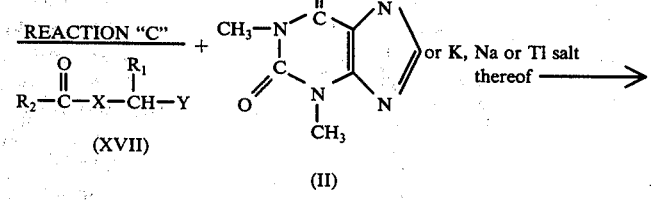

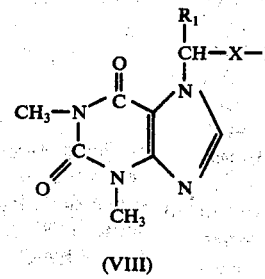

(VIII)

(1) $R_1$ and $R_2$ are as defined above.
(2) X and Y are as defined above.

In reaction "A", equimolar amounts of the compound of formula (IX) and (X) are reacted in the neat state in the presence of a Lewis acid catalyst such as $ZnCl_2$ or alternatively, in the presence of an organic solvent such as diethylether, dioxane, tetrahydrofuran, etc. The reaction is carried out at standard pressure, approximately 100° C, and over a period of time ranging from one to 24 hours. The product obtained from this reaction, i.e., the compound of formula (XI) is isolated via crystallization or fractional distillation from a suitable organic solvent such as hexane, heptane, benzene, etc.

In reaction "B", equimolar amounts of the compound of formula (XII) and (XIII) are reacted in the neat state under the same conditions and environment noted above in reaction "A" with the exception that the need for a Lewis acid catalyst does not exist. The compound obtained [the compound of formula (XIV)] is isolated via fractional distillation or crystallization. This compound is then reacted with $PCl_5$, $PBr_5$ or $PI_5$ at standard pressure, room temperature, and over a period of time ranging from one to 24 hours to obtain the compound of formula (XVI).

In reaction "C", the compounds of formula (XI) and (XVI) are then reacted with theophylline or the K, Na or Tl salt thereof in the presence of a suitable organic solvent such as acetone, dimethylformamide, tetrahydrofuran, etc., at standard pressure, over a temperature range of from 0° C to the boiling point of the solvent, over a period of from one to 24 hours, and further, in the presence of trimethylamine, triethylamine, or any other equivalent organic base.

As for the remaining compounds of the above-described generic formula, they can be prepared in accordance with the reaction scheme outlined below:

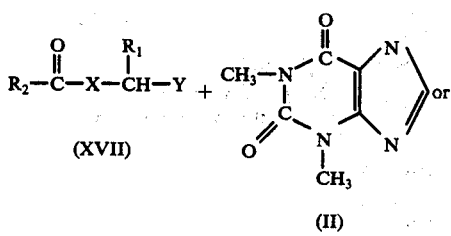

(XVII)                    (II)

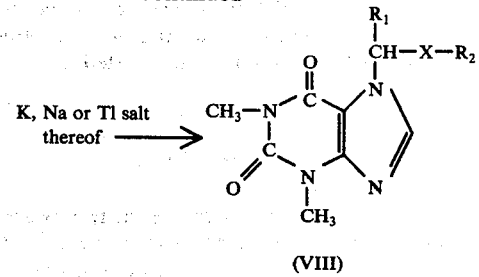

(VIII)

(1) $R_1$ and $R_2$ are as defined above.
(2) X and Y are as defined above.

The above reaction is carried out under the same conditions and environment described for reaction "B" of the alternative reaction procedure for preparing the majority of the compounds encompassed within the above-described generic formula noted above.

Without further elaboration, it is believed that one of ordinary skill in the art can, using the preceding description, utilize the instant invention to its utmost extent. The following preferred specific embodiments are, therefore, to be construed as merely illustrative, and not limitative of the remainder of the specification and claims in any way whatsoever. All references to "temperature" in the following examples denote Centigrade.

EXAMPLE I

Preparation of 7-Ethoxymethyl theophylline

A suspension of 7.20 g (0.04 mole) of theophylline and 2.76 g (0.02 mole) of $K_2CO_3$ in 200 ml of acetone was refluxed for two days and subsequently refluxed with 4.40 g (0.046 mole) of ethoxymethyl chloride for two days more. The suspension was filtered and the filtrate was concentrated in vacuo.

The residue was chromatographed on silica gel using diethyletheracetone (50:1) to acetone as the eluents. The first fraction that was obtained was the desired 7-ethoxymethyl theophylline (3.43 g, mp 110°–112° C, 35% yield). The product was recrystallized from dichloromethaneheptane to give 2.80 g (mp 111°–113° C) of 7-ethoxymethyl theophylline which had the correct elemental analysis.

Anal. Calcd for $C_{10}H_{14}N_4O_3$: C, 50.41; H, 5.92; N, 23.52;

Found: C, 50.59; H, 5.99; N, 23.58.

EXAMPLE II

Preparation of 7-Pivaloxymethyl theophylline

A suspension of 3.60 g (0.02 mole) of theophylline and 1.38 g (0.01 mole) of $K_2CO_3$ in 75 ml of acetone was refluxed overnight and then allowed to react at reflux with 3.00 g (0.02 mole) of pivaloxymethyl chloride for 2 days. The suspension was filtered and the residue was washed with acetone (200 ml). The combined filtrate and wash was concentrated in vacuo and the residue was extracted with boiling heptane (200 ml). The heptane solution was cooled in the refrigerator for 0.5 hr then filtered. The residue was dried in vacuo to give 1.50 g (mp 108°–109.5°) of 7-pivaloxymethyl theophylline.

Anal. Calcd for $C_{13}H_{18}N_4O_4$: C, 53.05; H, 6.16; N, 19.04;

Found: C, 53.06; H, 6.20; N, 19.32.

EXAMPLE III

Preparation of 7-(1-pyridyl)methyl theophylline chloride

A suspension of 3.60 g (0.02 mole) of theophylline, 2.30 g (0.02 mole) of pyridine hydrochloride and 0.7 g (0.023 mole) of paraformaldehyde was heated at 80° for 24 hr. Upon cooling, crystals immediately formed in the solution. The crystals were filtered and dried in vacuo to give 4.83 g (28% yield) of the desired compound as its hydrate.

Anal. Calcd for $C_{13}H_{14}N_5O_2Cl.H_2O$: C, 47.93; H, 4.95; N, 21.50;

Found: C, 47.89; H, 4.98, N, 21.61.

EXAMPLE IV

Preparation of 7-Hexanoyloxymethyl theophylline

To 0.71 g (0.0053 mole) of hexanoyl chloride in 10 ml of $CH_2Cl_2$ there was added 1.10 g (0.0052 mole) of 7-hydroxymethyl theophylline; no reaction occurred and the reaction mixture was a suspension. Then 0.58 g (0.0057 mole) of triethylamine was added and a clear, colorless solution was obtained. The solution was stirred at room temperature for 15 minutes then concentrated in vacuo. The residue was titrated with 200 ml ether and filtered. The filtrate was concentrated in vacuo to give an oil which was titrated with heptane $CH_2Cl_2$(50:10). The resulting suspension was filtered while hot and concentrated to 20 ml, then cooled to room temperature. A gelatinous mass precipitated which was filtered and dried to give 0.70 g (mp 67°–72° C, 43% yield) of the desired product.

Anal. Calcd for $C_{14}H_{20}N_4O_4$: C, 54.53, H, 6.54; N, 18.17;

Found: C, 54.58; H, 6.53; N, 18.35.

By following the preceding examples and substituting the appropriate generically or specifically described reactants and/or operating conditions of the instant invention, the following additional compounds were prepared:

1. 7-Octanoyloxymethyl theophylline: 46% yield, mp 79°–82°. Anal. Calcd for $C_{16}H_{24}N_4O_4$: C, 57.13; H, 7.19; N, 16.66; Found: C, 56.91; H, 7.23; N, 17.03.

2. 7-Butanoyloxymethyl theophylline: 44% yield, mp 104°–105°. Anal. Calcd for $C_{12}H_{16}N_4O_4$: C, 51.42; H, 5.68; N, 19.99; Found. C, 51.11; H, 5,80; N, 20.35.

3. 7-Ethoxycarbonoyloxymethyl theophylline: 33% yield, mp 126.5°–127.5°. Anal. Calcd for $C_{11}H_{14}N_4O_5$: C, 46.81; H, 5.00; N, 19.85; Found: C, 46.53; H, 4.99; N, 20.07.

EXAMPLE V

Preparation of 7-(N,N-diethylsuccinamyloxymethyl)theophylline

To a mixture of 0.86 g (0.005 mole) of the diethylamide of succinic acid was added 1.05 g (0.005 mole) of 7-hydroxymethyl theophylline and 1.1 g (0.0055 mole) of dicyclohexylcarbodiimide in 10 ml of $CH_2Cl_2$ and 1.5 ml of pyridine. The suspension was stirred at room temperature overnight then filtered. The filtrate was concentrated in vacuo to give an oil. The oil was crystallized from diethylether to give the product as white crystals, mp 100°–103° C.

Anal. Calcd for $C_{16}H_{23}N_5O_5$: C, 52.29; H, 6.34; N, 19.44; Found: C, 52.28; H, 6.22; N, 19.35.

EXAMPLE VI

Preparation of 7-(N,N-Dimethylglycyloxymethyl)theophylline

To a mixture of 2.05 g (0.0097 mole) of 7-hydroxymethyl theophylline, 1.05 g (0.01 mole) of N,N-dimethylglycine and 2.25 g (0.011 mole) of dicyclohexylcarbodiimide was added 20 ml of pyridine; the resulting suspension was stirred at room temperature for 24 hr. The suspension was filtered and the filtrate was concentrated in vacuo to a solid residue. The residue was dissolved in $CH_2Cl_2$ (30 ml) and filtered. The $CH_2Cl_2$ solution was diluted with heptane (500 ml) until cloudy and allowed to sit at room temperature to crystallize. The crystals were filtered to give 2.00 g (mp 111°–113° C, 67% yield) of a light tan solid which was one spot upon analysis by thin layer chromatography (silica gel, acetone) and which had a nuclear magnetic resonance spectrum [$(CDCl_3)\delta$7.88 (s, 1, N—CH=N), 6.28 (s, 2, N—CH$_2$—O), 3.60 (s, 3, N—CH$_3$), 3.46 (s, 3, N—CH$_3$), 3.25 (s, 2, CH$_2$—N) and 2.37 (s, 6, N—CH$_3$)] that was consistent with the structure of the desired product.

In similar fashion, the remaining compounds of the present invention can be prepared with similar success by merely following the preceding examples and substituting the generically and/or specifically described reactants and/or operating conditions of this invention for those of the preceding examples. Thus, the following additional compounds can be prepared by following the above reaction scheme:

| | R | | | | |
|---|---|---|---|---|---|
| N' | N³ | X | R₁ | R₂ | |
| $CH_3$ | $CH_3$ | O | H | $n$-$C_3H_7$ | |
| $CH_3$ | $CH_3$ | O | H | $n$-$C_4H_9$ | |
| $CH_3$ | $CH_3$ | O | H | $i$-$C_4H_9$ | |
| $CH_3$ | $CH_3$ | O | H | $-CH_2-C_6H_5$ | |
| $CH_3$ | $CH_3$ | O | H | $-CH_2-N(CH_3)_2$ | |
| $CH_3$ | $CH_3$ | O | H | $-CH_2-N(C_2H_5)_2$ | |
| $CH_3$ | $CH_3$ | O | H | $-CO-O-CH_2-C_6H_5$ | |
| $CH_3$ | $CH_3$ | O | H | $-CO-O-CH_2-CCl_3$ | |
| $CH_3$ | $CH_3$ | O | H | $-CO-CH_2-N(C_2H_5)_2$ | |
| $CH_3$ | $CH_3$ | O | H | $-CO-CH_2-N\text{(piperidine)}$ | |
| $CH_3$ | $CH_3$ | O | H | $-CO-C_6H_5$ | |
| $CH_3$ | $CH_3$ | O | H | $-CO-C_6H_4-CH_3$ | |
| $CH_3$ | $CH_3$ | O | H | $-CO-C_6H_4-OCH_3$ | |
| $CH_3$ | $CH_3$ | O | H | $-CO-C_6H_4-N(CH_3)_2$ | |
| $CH_3$ | $CH_3$ | O | H | $-CO-CH_2-C_6H_5$ | |
| $CH_3$ | $CH_3$ | O | H | $-CO-\text{(2-pyridyl)}$ | |
| $CH_3$ | $CH_3$ | O | H | $-CO-\text{(pyridyl)}$ | |
| $CH_3$ | $CH_3$ | O | H | $-CO-CH_2-NH-HCO$ | |
| $CH_3$ | $CH_3$ | O | H | $-CO-CH_2-NH-CO-O-CH_2-C_6H_5$ | |
| $CH_3$ | $CH_3$ | O | H | $-CO-CH_2-NH-CO-O-C_2H_5$ | |
| $CH_3$ | $CH_3$ | O | H | $-CO-CH=CH-C_6H_5$ | |
| $CH_3$ | $CH_3$ | O | H | $-CO-CH_2-CH_2-COOCH_3$ | |
| $CH_3$ | $CH_3$ | O | H | $-CO-CH_2-CH_2-CON(CH_3)_2$ | |
| $CH_3$ | $CH_3$ | O | H | $-CO-CH_2-\overset{\oplus}{N}(CH_3)_3 \cdot Y$ (Y=Cl, Br, I, etc.) | |
| $CH_3$ | $CH_3$ | O | H | $-CO-CH_2-\overset{\oplus}{N}(C_2H_5)_3 \cdot Y$ (Y=Cl, Br, I, etc.) | |
| $CH_3$ | $CH_3$ | O | H | $-C_2H_4-N(CH_3)_2\text{-pyridyl}$ | |
| $CH_3$ | $CH_3$ | O | H | $-CO-\text{(pyridyl N-oxide)}$ | |
| $CH_3$ | $CH_3$ | O | H | $-SO_2-C_6H_4-CH_3$ | |

-continued

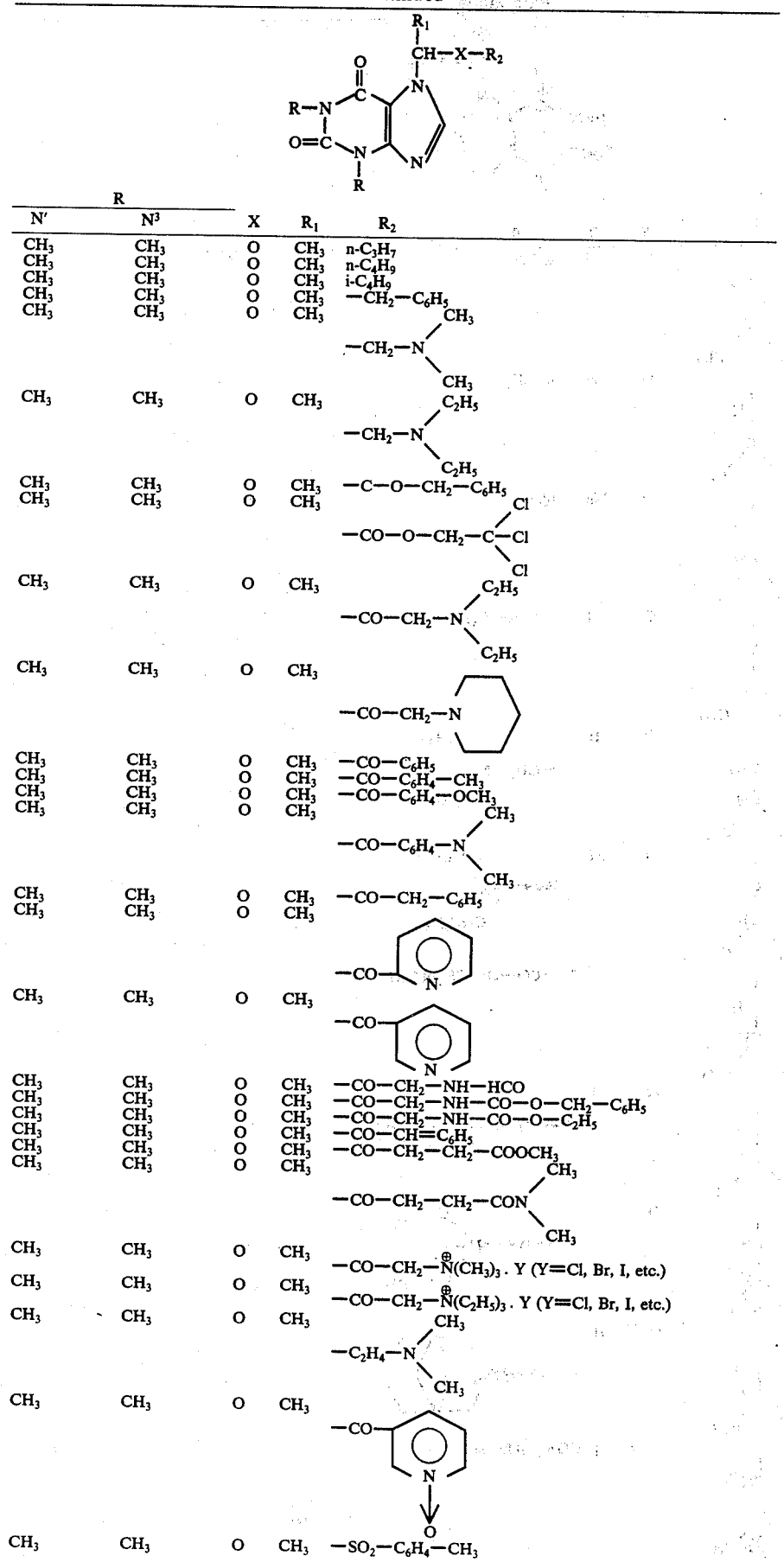

| | R | | | | |
|---|---|---|---|---|---|
| N' | N³ | X | R₁ | R₂ | |
| $CH_3$ | $CH_3$ | O | $CH_3$ | $n-C_3H_7$ | |
| $CH_3$ | $CH_3$ | O | $CH_3$ | $n-C_4H_9$ | |
| $CH_3$ | $CH_3$ | O | $CH_3$ | $i-C_4H_9$ | |
| $CH_3$ | $CH_3$ | O | $CH_3$ | $-CH_2-C_6H_5$ | |
| $CH_3$ | $CH_3$ | O | $CH_3$ | $-CH_2-N(CH_3)_2$ | |
| $CH_3$ | $CH_3$ | O | $CH_3$ | $-CH_2-N(C_2H_5)_2$ | |
| $CH_3$ | $CH_3$ | O | $CH_3$ | $-C-O-CH_2-C_6H_5$ | |
| $CH_3$ | $CH_3$ | O | $CH_3$ | $-CO-O-CH_2-CCl_3$ | |
| $CH_3$ | $CH_3$ | O | $CH_3$ | $-CO-CH_2-N(C_2H_5)_2$ | |
| $CH_3$ | $CH_3$ | O | $CH_3$ | $-CO-CH_2-N(\text{piperidine})$ | |
| $CH_3$ | $CH_3$ | O | $CH_3$ | $-CO-C_6H_5$ | |
| $CH_3$ | $CH_3$ | O | $CH_3$ | $-CO-C_6H_4-CH_3$ | |
| $CH_3$ | $CH_3$ | O | $CH_3$ | $-CO-C_6H_4-OCH_3$ | |
| $CH_3$ | $CH_3$ | O | $CH_3$ | $-CO-C_6H_4-N(CH_3)_2$ | |
| $CH_3$ | $CH_3$ | O | $CH_3$ | $-CO-CH_2-C_6H_5$ | |
| $CH_3$ | $CH_3$ | O | $CH_3$ | $-CO-(3\text{-pyridyl})$ | |
| $CH_3$ | $CH_3$ | O | $CH_3$ | $-CO-(4\text{-pyridyl})$ | |
| $CH_3$ | $CH_3$ | O | $CH_3$ | $-CO-CH_2-NH-HCO$ | |
| $CH_3$ | $CH_3$ | O | $CH_3$ | $-CO-CH_2-NH-CO-O-CH_2-C_6H_5$ | |
| $CH_3$ | $CH_3$ | O | $CH_3$ | $-CO-CH_2-NH-CO-O-C_2H_5$ | |
| $CH_3$ | $CH_3$ | O | $CH_3$ | $-CO-CH=C_6H_5$ | |
| $CH_3$ | $CH_3$ | O | $CH_3$ | $-CO-CH_2-CH_2-COOCH_3$ | |
| $CH_3$ | $CH_3$ | O | $CH_3$ | $-CO-CH_2-CH_2-CON(CH_3)_2$ | |
| $CH_3$ | $CH_3$ | O | $CH_3$ | $-CO-CH_2-\overset{\oplus}{N}(CH_3)_3 \cdot Y$ (Y=Cl, Br, I, etc.) | |
| $CH_3$ | $CH_3$ | O | $CH_3$ | $-CO-CH_2-\overset{\oplus}{N}(C_2H_5)_3 \cdot Y$ (Y=Cl, Br, I, etc.) | |
| $CH_3$ | $CH_3$ | O | $CH_3$ | $-C_2H_4-N(CH_3)_2$ | |
| $CH_3$ | $CH_3$ | O | $CH_3$ | $-CO-(4\text{-pyridyl N-oxide})$ | |
| $CH_3$ | $CH_3$ | O | $CH_3$ | $-SO_2-C_6H_4-CH_3$ | |

-continued

[Structure: xanthine core with N' substituted by -CH(R₁)-X-R₂, N3 substituted by R, and two R groups on the other nitrogens]

| R | | X | R₁ | R₂ |
|---|---|---|---|---|
| N' | N³ | | | |
| CH₃ | -CH₂-CH(CH₃)-CH₃ (isobutyl) | O | H | n-C₃H₇ |
| CH₃ | -CH₂-CH(CH₃)-CH₃ | O | H | n-C₄H₉ |
| CH₃ | -CH₂-CH(CH₃)-CH₃ | O | H | i-C₄H₉ |
| CH₃ | -CH₂-CH(CH₃)-CH₃ | O | H | —CH₂—C₆H₅ |
| CH₃ | -CH₂-CH(CH₃)-CH₃ | O | H | —CH₂—N(CH₃)₂ |
| CH₃ | -CH₂-CH(CH₃)-CH₃ | O | H | —CH₂—N(C₂H₅)₂ |
| CH₃ | -CH₂-CH(CH₃)-CH₃ | O | H | —CO—O—CH₂—C₆H₅ |
| CH₃ | -CH₂-CH(CH₃)-CH₃ | O | H | —CO—O—CH₂—CCl₃ |
| CH₃ | -CH₂-CH(CH₃)-CH₃ | O | H | —CO—CH₂—N(C₂H₅)₂ |
| CH₃ | -CH₂-CH(CH₃)-CH₃ | O | H | —CO—CH₂—N(piperidinyl) |
| CH₃ | -CH₂-CH(CH₃)-CH₃ | O | H | —CO—C₆H₅ |

-continued

![structure: 7-substituted xanthine with R on N1,N3; CH(R1)-X-R2 on N7]

| N' | R N³ | X | R₁ | R₂ |
|---|---|---|---|---|
| CH₃ | -CH₂-CH(CH₃)₂ | O | H | -CO-C₆H₄-CH₃ |
| CH₃ | -CH₂-CH(CH₃)₂ | O | H | -CO-C₆H₄-OCH₃ |
| CH₃ | -CH₂-CH(CH₃)₂ | O | H | -CO-C₆H₄-N(CH₃)₂ |
| CH₃ | -CH₂-CH(CH₃)₂ | O | H | -CO-CH₂-C₆H₅ |
| CH₃ | -CH₂-CH(CH₃)₂ | O | H | -CO-(2-pyridyl) |
| CH₃ | -CH₂-CH(CH₃)₂ | O | H | -CO-(3-pyridyl) |
| CH₃ | -CH₂-CH(CH₃)₂ | O | H | -CO-CH₂-NH-HCO |
| CH₃ | -CH₂-CH(CH₃)₂ | O | H | -CO-CH₂-NH-CO-O-CH₂-C₆H₅ |
| CH₃ | -CH₂-CH(CH₃)₂ | O | H | -CO-CH₂-NH-CO-O-C₂H₅ |
| CH₃ | -CH₂-CH(CH₃)₂ | O | H | -CO-CH=CH-C₆H₅ |
| CH₃ | -CH₂-CH(CH₃)₂ | O | H | -CO-CH₂-CH₂-COOCH₃ |

-continued $$\text{structure with } R_1, X, R_2 \text{ substituents on xanthine}$$

| R N' | R N³ | X | $R_1$ | $R_2$ |
|---|---|---|---|---|
| $CH_3$ | $-CH_2-CH(CH_3)_2$ | O | H | $-CO-CH_2-CH_2-CON(CH_3)_2$ |
| $CH_3$ | $-CH_2-CH(CH_3)_2$ | O | H | $-CO-CH_2-\overset{\oplus}{N}(CH_3)_3 \cdot Y$ (Y=Cl, Br, I, etc.) |
| $CH_3$ | $-CH_2-CH(CH_3)_2$ | O | H | $-CO-CH_2-\overset{\oplus}{N}(C_2H_5)_3 \cdot Y$ (Y=Cl, Br, I, etc.) |
| $CH_3$ | $-CH_2-CH(CH_3)_2$ | O | H | $-C_2H_4-N(CH_3)_2$ |
| $CH_3$ | $-CH_2-CH(CH_3)_2$ | O | H | $-CO-$ (pyridyl N-oxide) |
| $CH_3$ | $-CH_2-CH(CH_3)_2$ | O | H | $-SO_2-C_6H_4-CH_3$ |
| $CH_3$ | $-CH_2-CH(CH_3)_2$ | O | $CH_3$ | $n-C_3H_7$ |
| $CH_3$ | $-CH_2-CH(CH_3)_2$ | O | $CH_3$ | $n-C_4H_9$ |
| $CH_3$ | $-CH_2-CH(CH_3)_2$ | O | $CH_3$ | $i-C_4H_9$ |
| $CH_3$ | $-CH_2-CH(CH_3)_2$ | O | $CH_3$ | $-CH_2-C_6H_5$ |

-continued

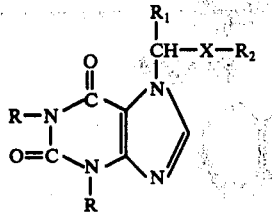

| R N' | R N³ | X | R₁ | R₂ |
|---|---|---|---|---|
| CH₃ | —CH₂—CH(CH₃)—CH₃ | O | CH₃ | —CH₂—N(CH₃)₂ |
| CH₃ | —CH₂—CH(CH₃)—CH₃ | O | CH₃ | —CH₂—N(C₂H₅)₂ |
| CH₃ | —CH₂—CH(CH₃)—CH₃ | O | CH₃ | —CO—O—CH₂—C₆H₅ |
| CH₃ | —CH₂—CH(CH₃)—CH₃ | O | CH₃ | —CO—O—CH₂—CCl₃ |
| CH₃ | —CH₂—CH(CH₃)—CH₃ | O | CH₃ | —CO—CH₂—N(C₂H₅)₂ |
| CH₃ | —CH₂—CH(CH₃)—CH₃ | O | CH₃ | —CO—CH₂—N(piperidinyl) |
| CH₃ | —CH₂—CH(CH₃)—CH₃ | O | CH₃ | —CO—C₆H₅ |
| CH₃ | —CH₂—CH(CH₃)—CH₃ | O | CH₃ | —CO—C₆H₄—CH₃ |
| CH₃ | —CH₂—CH(CH₃)—CH₃ | O | CH₃ | —CO—C₆H₄—OCH₃ |
| CH₃ | —CH₂—CH(CH₃)—CH₃ | O | CH₃ | —CO—C₆H₄—N(CH₃)₂ |
| CH₃ | —CH₂—CH(CH₃)—CH₃ | O | CH₃ | —CO—CH₂—C₆H₅ |

-continued

| R N' | R N³ | X | R₁ | R₂ |
|---|---|---|---|---|
| $CH_3$ | $-CH_2-CH(CH_3)_2$ | O | $CH_3$ | —CO—(2-pyridyl) |
| $CH_3$ | $-CH_2-CH(CH_3)_2$ | O | $CH_3$ | —CO—(3-pyridyl) |
| $CH_3$ | $-CH_2-CH(CH_3)_2$ | O | $CH_3$ | $-CO-CH_2-NH-HCO$ |
| $CH_3$ | $-CH_2-CH(CH_3)_2$ | O | $CH_3$ | $-CO-CH_2-NH-CO-O-CH_2-C_6H_5$ |
| $CH_3$ | $-CH_2-CH(CH_3)_2$ | O | $CH_3$ | $-CO-CH_2-NH-CO-O-C_2H_5$ |
| $CH_3$ | $-CH_2-CH(CH_3)_2$ | O | $CH_3$ | $-CO-CH=CH-C_6H_5$ |
| $CH_3$ | $-CH_2-CH(CH_3)_2$ | O | $CH_3$ | $-CO-CH_2-CH_2-COOCH_3$ |
| $CH_3$ | $-CH_2-CH(CH_3)_2$ | O | $CH_3$ | $-CO-CH_2-CH_2-CON(CH_3)_2$ |
| $CH_3$ | $-CH_2-CH(CH_3)_2$ | O | $CH_3$ | $-CO-CH_2-\overset{\oplus}{N}(CH_3)_3 \cdot Y$ (Y=Cl, Br, I, etc.) |
| $CH_3$ | $-CH_2-CH(CH_3)_2$ | O | $CH_3$ | $-CO-CH_2-\overset{\oplus}{N}(C_2H_5)_3 \cdot Y$ (Y=Cl, Br, I, etc.) |
| $CH_3$ | $-CH_2-CH(CH_3)_2$ | O | $CH_3$ | $-C_2H_4-N(CH_3)_2$ |

-continued

[Structure: xanthine-like core with N substituted by R (at N1, N3), and N7 substituted by -CH(R1)-X-R2]

| N' | N³ | X | R₁ | R₂ |
|---|---|---|---|---|
| CH₃ | -CH₂-CH(CH₃)₂ | O | CH₃ | -CO- (4-pyridyl N-oxide) |
| CH₃ | -CH₂-CH(CH₃)₂ | O | CH₃ | -SO₂-C₆H₄-CH₃ |
| CH₃ | CH₃ | S | H | n-C₃H₇ |
| CH₃ | CH₃ | S | H | n-C₄H₉ |
| CH₃ | CH₃ | S | H | i-C₄H₉ |
| CH₃ | CH₃ | S | H | -CH₂-C₆H₅ |
| CH₃ | CH₃ | S | H | -CH₂-N(CH₃)₂ |
| CH₃ | CH₃ | S | H | -CH₂-N(C₂H₅)₂ |
| CH₃ | CH₃ | S | H | -CO-O-CH₂-C₆H₅ |
| CH₃ | CH₃ | S | H | -CO-O-CH₂-CCl₃ |
| CH₃ | CH₃ | S | H | -CO-CH₂-N(C₂H₅)₂ |
| CH₃ | CH₃ | S | H | -CO-CH₂-N(piperidyl) |
| CH₃ | CH₃ | S | H | -CO-C₆H₅ |
| CH₃ | CH₃ | S | H | -CO-C₆H₄-CH₃ |
| CH₃ | CH₃ | S | H | -CO-C₆H₄-OCH₃ |
| CH₃ | CH₃ | S | H | -CO-C₆H₄-N(CH₃)₂ |
| CH₃ | CH₃ | S | H | -CO-CH₂-C₆H₅ |
| CH₃ | CH₃ | S | H | -CO-(2-piperidyl) |
| CH₃ | CH₃ | S | H | -CO-(3-piperidyl) |
| CH₃ | CH₃ | S | H | -CO-CH₂-NH-HCO |
| CH₃ | CH₃ | S | H | -CO-CH₂-NH-CO-O-CH₂-C₆H₅ |
| CH₃ | CH₃ | S | H | -CO-CH₂-NH-CO-O-C₂H₅ |
| CH₃ | CH₃ | S | H | -CO-CH=CH-C₆H₅ |
| CH₃ | CH₃ | S | H | -CO-CH₂-CH₂-COOCH₃ |
| CH₃ | CH₃ | S | H | -CO-CH₂-CH₂-CON(CH₃)₂ |
| CH₃ | CH₃ | S | H | -CO-CH₂-N⁺(CH₃)₃ · Y⁻ (Y=Cl, Br, I, etc.) |

-continued

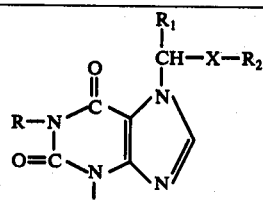

| R N' | R N³ | X | R₁ | R₂ |
|---|---|---|---|---|
| CH₃ | CH₃ | S | H | $-CO-CH_2-\overset{\oplus}{N}(C_2H_5)_3 \cdot Y$ (Y=Cl, Br, I, etc.) |
| CH₃ | CH₃ | S | H | $-C_2H_4-N\begin{smallmatrix}CH_3\\CH_3\end{smallmatrix}$ |
| CH₃ | CH₃ | S | H | $-CO-$ (4-pyridyl N-oxide) |
| CH₃ | CH₃ | S | H | $-SO_2-C_6H_4-CH_3$ |
| CH₃ | CH₃ | S | CH₃ | n-C₃H₇ |
| CH₃ | CH₃ | S | CH₃ | n-C₄H₉ |
| CH₃ | CH₃ | S | CH₃ | i-C₄H₉ |
| CH₃ | CH₃ | S | CH₃ | $-CH_2-C_6H_5$ |
| CH₃ | CH₃ | S | CH₃ | $-CH_2-N\begin{smallmatrix}CH_3\\CH_3\end{smallmatrix}$ |
| CH₃ | CH₃ | S | CH₃ | $-CH_2-N\begin{smallmatrix}C_2H_5\\C_2H_5\end{smallmatrix}$ |
| CH₃ | CH₃ | S | CH₃ | $-CO-O-CH_2-C_6H_5$ |
| CH₃ | CH₃ | S | CH₃ | $-CO-O-CH_2-CCl_3$ |
| CH₃ | CH₃ | S | CH₃ | $-CO-CH_2-N\begin{smallmatrix}C_2H_5\\C_2H_5\end{smallmatrix}$ |
| CH₃ | CH₃ | S | CH₃ | $-CO-CH_2-N$(piperidine) |
| CH₃ | CH₃ | S | CH₃ | $-CO-C_6H_5$ |
| CH₃ | CH₃ | S | CH₃ | $-CO-C_6H_4-CH_3$ |
| CH₃ | CH₃ | S | CH₃ | $-CO-C_6H_4-OCH_3$ |
| CH₃ | CH₃ | S | CH₃ | $-CO-C_6H_4-N\begin{smallmatrix}CH_3\\CH_3\end{smallmatrix}$ |
| CH₃ | CH₃ | S | CH₃ | $-CO-CH_2-C_6H_5$ |
| CH₃ | CH₃ | S | CH₃ | $-CO-$(2-pyridyl) |
| CH₃ | CH₃ | S | CH₃ | $-CO-$(4-pyridyl) |
| CH₃ | CH₃ | S | CH₃ | $-CO-CH_2-NH-HCO$ |
| CH₃ | CH₃ | S | CH₃ | $-CO-CH_2-NH-CO-O-CH_2-C_6H_5$ |
| CH₃ | CH₃ | S | CH₃ | $-CO-CH_2-NH-CO-O-C_2H_5$ |
| CH₃ | CH₃ | S | CH₃ | $-CO-CH=CH-C_6H_5$ |
| CH₃ | CH₃ | S | CH₃ | $-CO-CH_2-CH_2-COOCH_3$ |
| CH₃ | CH₃ | S | CH₃ | $-CO-CH_2-CH_2-CON\begin{smallmatrix}CH_3\\CH_3\end{smallmatrix}$ |
| CH₃ | CH₃ | S | CH₃ | $-CO-CH_2-\overset{\oplus}{N}(CH_3)_3 \cdot Y$ (Y=Cl Br, I. etc.) |

-continued

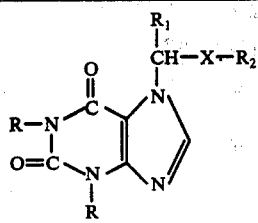

| N' | N³ | X | R₁ | R₂ |
|---|---|---|---|---|
| CH₃ | CH₃ | S | CH₃ | $-CO-CH_2-\overset{\oplus}{N}(C_2H_5)_3 \cdot Y$ (Y=Cl, Br, I, etc.) |
| CH₃ | CH₃ | S | CH₃ | $-C_2H_4-N\begin{matrix}CH_3\\CH_3\end{matrix}$ |
| CH₃ | CH₃ | S | CH₃ | ![pyridine N-oxide carbonyl] $-CO-$(pyridine N-oxide) |
| CH₃ | CH₃ | S | CH₃ | $-SO_2-C_6H_4-CH_3$ |
| CH₃ | $-CH_2-CH(CH_3)_2$ | S | H | n-C₃H₇ |
| CH₃ | $-CH_2-CH(CH_3)_2$ | S | H | n-C₄H₉ |
| CH₃ | $-CH_2-CH(CH_3)_2$ | S | H | i-C₄H₉ |
| CH₃ | $-CH_2-CH(CH_3)_2$ | S | H | $-CH_2-C_6H_5$ |
| CH₃ | $-CH_2-CH(CH_3)_2$ | S | H | $-CH_2-N(CH_3)_2$ |
| CH₃ | $-CH_2-CH(CH_3)_2$ | S | H | $-CH_2-N(C_2H_5)_2$ |
| CH₃ | $-CH_2-CH(CH_3)_2$ | S | H | $-CO-O-CH_2-C_6H_5$ |
| CH₃ | $-CH_2-CH(CH_3)_2$ | S | H | $-CO-O-CH_2-CCl_3$ |

-continued $$\text{Structure with } R_1, R_2, X, R \text{ on xanthine core}$$

| R (N') | R (N³) | X | R₁ | R₂ |
|---|---|---|---|---|
| CH₃ | —CH₂—CH(CH₃)₂ | S | H | —CO—CH₂—N(C₂H₅)₂ |
| CH₃ | —CH₂—CH(CH₃)₂ | S | H | —CO—CH₂—N(piperidine) |
| CH₃ | —CH₂—CH(CH₃)₂ | S | H | —CO—C₆H₅ |
| CH₃ | —CH₂—CH(CH₃)₂ | S | H | —CO—C₆H₄—CH₃ |
| CH₃ | —CH₂—CH(CH₃)₂ | S | H | —CO—C₆H₄—OCH₃ |
| CH₃ | —CH₂—CH(CH₃)₂ | S | H | —CO—C₆H₄—N(CH₃)₂ |
| CH₃ | —CH₂—CH(CH₃)₂ | S | H | —CO—CH₂—C₆H₅ |
| CH₃ | —CH₂—CH(CH₃)₂ | S | H | —CO—(2-pyridyl) |
| CH₃ | —CH₂—CH(CH₃)₂ | S | H | —CO—(3-pyridyl) |
| CH₃ | —CH₂—CH(CH₃)₂ | S | H | —CO—CH₂—NH—HCO |
| CH₃ | —CH₂—CH(CH₃)₂ | S | H | —CO—CH₂—NH—CO—O—CH₂—C₆H₅ |

-continued $$\text{structure with } R_1, R_2, X, R \text{ substituents on xanthine skeleton}$$

| | R | X | R₁ | R₂ |
|---|---|---|---|---|
| N' | N³ | | | |
| CH₃ | CH₂-CH(CH₃)₂ (isobutyl) | S | H | —CO—CH₂—NH—CO—O—C₂H₅ |
| CH₃ | isobutyl | S | H | —CO—CH=CH—C₆H₅ |
| CH₃ | isobutyl | S | H | —CO—CH₂—CH₂—COOCH₃ |
| CH₃ | isobutyl | S | H | —CO—CH₂—CH₂—CON(CH₃)₂ |
| CH₃ | isobutyl | S | H | —CO—CH₂—$\overset{\oplus}{N}$(CH₃)₃ · Y (Y=Cl, Br, I, etc.) |
| CH₃ | isobutyl | S | H | —CO—CH₂—$\overset{\oplus}{N}$(C₂H₅)₃ · Y (Y=Cl, Br, I, etc.) |
| CH₃ | isobutyl | S | H | —C₂H₄—N(CH₃)₂ |
| CH₃ | isobutyl | S | H | —CO—(pyridine N-oxide) |
| CH₃ | isobutyl | S | H | —SO₂—C₆H₄—CH₃ |
| CH₃ | isobutyl | S | CH₃ | n-C₃H₇ |

-continued
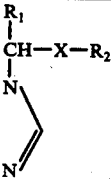
| N' | R N³ | X | R₁ | R₂ |
|---|---|---|---|---|
| CH₃ | -CH₂-CH(CH₃)₂ | S | CH₃ | n-C₄H₉ |
| CH₃ | -CH₂-CH(CH₃)₂ | S | CH₃ | i-C₄H₉ |
| CH₃ | -CH₂-CH(CH₃)₂ | S | CH₃ | -CH₂-C₆H₅ |
| CH₃ | -CH₂-CH(CH₃)₂ | S | CH₃ | -CH₂-N(CH₃)₂ |
| CH₃ | -CH₂-CH(CH₃)₂ | S | CH₃ | -CH₂-N(C₂H₅)₂ |
| CH₃ | -CH₂-CH(CH₃)₂ | S | CH₃ | -CO-O-CH₂-C₆H₅ |
| CH₃ | -CH₂-CH(CH₃)₂ | S | CH₃ | -CO-O-CH₂-CCl₃ |
| CH₃ | -CH₂-CH(CH₃)₂ | S | CH₃ | -CO-CH₂-N(C₂H₅)₂ |
| CH₃ | -CH₂-CH(CH₃)₂ | S | CH₃ | -CO-CH₂-N(piperidine) |
| CH₃ | -CH₂-CH(CH₃)₂ | S | CH₃ | -CO-C₆H₅ |
| CH₃ | -CH₂-CH(CH₃)₂ | S | CH₃ | -CO-C₆H₄-CH₃ |

-continued

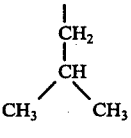

| R N' | R N³ | X | R₁ | R₂ |
|---|---|---|---|---|
| $CH_3$ | $-CH_2-CH(CH_3)_2$ | S | $CH_3$ | $-CO-C_6H_4-OCH_3$ |
| $CH_3$ | $-CH_2-CH(CH_3)_2$ | S | $CH_3$ | $-CO-C_6H_4-N(CH_3)_2$ |
| $CH_3$ | $-CH_2-CH(CH_3)_2$ | S | $CH_3$ | $-CO-CH_2-C_6H_5$ |
| $CH_3$ | $-CH_2-CH(CH_3)_2$ | S | $CH_3$ | $-CO-\text{(2-pyridyl)}$ |
| $CH_3$ | $-CH_2-CH(CH_3)_2$ | S | $CH_3$ | $-CO-\text{(3-pyridyl)}$ |
| $CH_3$ | $-CH_2-CH(CH_3)_2$ | S | $CH_3$ | $-CO-CH_2-NH-HCO$ |
| $CH_3$ | $-CH_2-CH(CH_3)_2$ | S | $CH_3$ | $-CO-CH_2-NH-CO-O-CH_2-C_6H_5$ |
| $CH_3$ | $-CH_2-CH(CH_3)_2$ | S | $CH_3$ | $-CO-CH_2-NH-CO-O-C_2H_5$ |
| $CH_3$ | $-CH_2-CH(CH_3)_2$ | S | $CH_3$ | $-CO-CH=CH-C_6H_5$ |
| $CH_3$ | $-CH_2-CH(CH_3)_2$ | S | $CH_3$ | $-CO-CH_2-CH_2-COOCH_3$ |
| $CH_3$ | $-CH_2-CH(CH_3)_2$ | S | $CH_3$ | $-CO-CH_2-CH_2-CON(CH_3)_2$ |

-continued

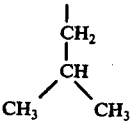

| N' | R N³ | X | R₁ | R₂ |
|---|---|---|---|---|
| CH₃ | —CH₂—CH(CH₃)—CH₃ (isobutyl) | S | CH₃ | $-CO-CH_2-\overset{\oplus}{N}(CH_3)_3 \cdot Y$ (Y=Cl, Br, I, etc.) |
| CH₃ | —CH₂—CH(CH₃)—CH₃ | S | CH₃ | $-CO-CH_2-\overset{\oplus}{N}(C_2H_5)_3 \cdot Y$ (Y=Cl, Br, I, etc.) |
| CH₃ | —CH₂—CH(CH₃)—CH₃ | S | CH₃ | $-C_2H_4-N(CH_3)_2$ |
| CH₃ | —CH₂—CH(CH₃)—CH₃ | S | CH₃ | 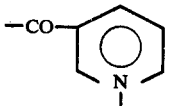 |
| CH₃ | —CH₂—CH(CH₃)—CH₃ | S | CH₃ | $-SO_2-C_6H_4-CH_3$ |

EXAMPLE VII

Partition Coefficient Studies

That the compounds of the instant invention are suitable for dermal application is established by determining their partition coefficient values in water/heptane versus water and heptane, per se, as illustrated in Table I below:

TABLE I

|  | Water mg/ml | $\overset{O}{\underset{\parallel}{thCH_2OC}}-R$<br>Heptane mg/ml | Water/Heptane |
|---|---|---|---|
| R = C₃H₇ | 3.89 | 0.65 | 6.30 |
| = C(CH₃)₃ | 2.01 | 1.55 | 1.11 |
| = C₅H₁₁ | 0.11 | 2.26 | 0.42 |
| = C₇H₁₅ | 0.12 | 0.52 | 0.06 |
| = C₂H₅ | 3.87 | 0.18 | 32.0 |
| = CH₂N(CH₃)(CH₃) | >1 g/ml | <10 mg/500 ml | |
| = CH₂CH₂C(O)N(C₂H₅)(C₂H₅) | 26.3 | 0.17 | 25.0 | th = 7-theophylline

It is obvious from the foregoing Table that derivatives of selected xanthine compounds (e.g., theophylline) have been prepared with reasonable water and heptane solubilities and in most cases the partition coefficient is near unity.

Repeating the above partition studies with the remaining compounds of the present invention will yield partition coefficient values similar to those noted above.

The compounds of the present invention are conveniently administered to warm-blooded animals via topical administration with any suitable pharmaceutically acceptable topical carrier material. Such carrier materials are well known to those skilled in the art of topical pharmaceutical formulations. For those not skilled in the art, reference is made to the text entitled, "Remington's Pharmaceutical Sciences" (Fourteenth Edition), 1970 and U.S. Pat. No. 3,849,553. In a typical preparation for topical application, any one of the compounds of the instant invention is combined with triacetin such that the active ingredient approximates a concentration of from 1 to 5 percent. The preparation is simply applied topically to the psoriatic area whereby the therapeutically active compound is dermally absorbed and cleaved to release the parent xanthine moiety whereby cyclic AMP levels are increased resulting in an inhibition of phosphodiesterase activity. Naturally, the topical administrative regimen of the compounds of the instant application will vary with the degree of the psoratic condition being treated. As such, frequency of administration is left to the physician or individual being treated. The dosage administrated is not subject to definite bounds, but it will usually be an effective amount, or the equivalent on a molar basis of the pharmacologically active form produced upon the metabolic release of the active drug to achieve its desired pharmacological and physiological effect.

If necessary, ancillary adjuvants may be added to the above-described topical formulation such as coloring agents, scenting agents and the like with the proviso that such adjuvants do not detract from the main purpose of the present invention, i.e., do not impede dermal absorption of the presently described compounds.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably, and intended to be, within the full range of equivalence of the following claims.

What we claim is:

1. A method for topically treating psoriasis on a warm-blooded animal afflicted with the same which comprises topically administering thereto an antipsoriatic effective amount of a compound having the formula:

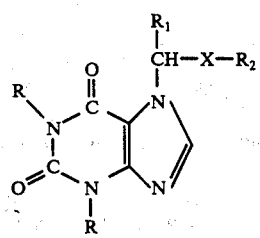

wherein R, which may be the same or different, represents a member selected from the group consisting of —CH$_3$, —C$_2$H$_5$, iso—C$_3$H$_7$, —C$_4$H$_9$, iso—C$_4$H$_9$, pentyl, benzyl, allyl, 2-hydroxyethyl, cyclohexyl, 2-isobutenyl, hydroxymethyl, 2-phenylethyl and —CH$_2$O$_{13R2}$, wherein R$_2$ is defined infra; wherein R$_1$ represents a member selected from the group consisting of H, C$_1$-C$_7$ straight or branched alky, CCl$_3$, CBr$_3$, CI$_3$,

CH$_3$O—CH$_2$—, (CH$_3$)$_2$NCH$_2$—, —CHO,

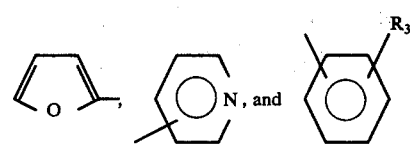

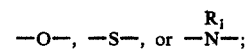

wherein R$_3$ represents a member selected from the group consisting of —OH, halogen, —OCH$_3$, —COOCH$_3$, —NO$_2$ and —OCOCH$_3$; wherein X is $$-O-, -S-, \text{ or } -\underset{R_1}{\overset{}{N}}-;$$

and wherein R$_2$ represents a member selected from the group consisting of

wherein R$_4$ is a member selected from the group consisting of C$_2$-C$_{20}$ straight or branched alkyl,

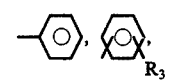

wherein R$_3$ is defined as above,

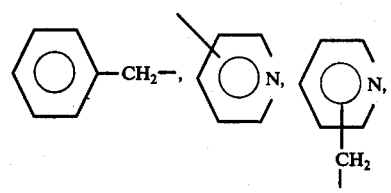

the residue of any naturally occurring amino acid, the residue of any N— substituted amino acid, wherein said substituent is any amino acid protective group cleavable via hydrogenolysis or hydrolysis the residue of an N,N—C$_1$—C$_5$—dialkyl or cycloalkylamino acid,

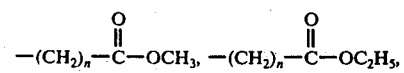

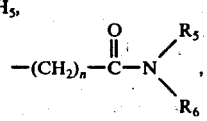

wherein n represents an integer of from 1-5 and $R_5$ and $R_6$ which may be the same or different represent $C_1$-$C_5$ alkyl or together form a heterocyclic ring with the N atom to which they are attached, imidazolyl, O—C$_1$—C$_8$ alkyl, O-benzyl, O-phenyl and

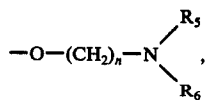

wherein n, $R_5$ and $R_6$ are defined as above; and wherein $R_2$ further represents a member selected from the group consisting of straight or branched $C_1$-$C_{20}$ alkyl,

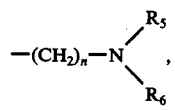

wherein n, $R_5$ and $R_6$ are defined as above, phenyl, tolyl, xylyl, and —$SO_2$—$R_7$, wherein $R_7$ is a straight or branched $C_1$-$C_{20}$ alkyl.

2. The method of claim 1 wherein said compound is: 7-Pivaloxymethyl theophylline.

3. The method of claim 1, wherein said compound is: 7-(Pyridinium chloride)methyl theophylline.

4. The method of claim 1, wherein said compound is: 7-Hexanoyloxymethyl theophylline.

5. The method of claim 1, wherein said compound is: 7-Octanoyloxymethyl theophylline.

6. The method of claim 1, wherein said compound is: 7-Butanoyloxymethyl theophylline.

7. The method of claim 1, wherein said compound is: 7-Ethoxycarbonoloxymethyl theophylline.

8. The method of claim 1, wherein said compound is: 7-(N,N-diethylamidosuccinyloxymethyl)theophylline.

9. The method of claim 1, wherein said compound is: 7-(N,N-dimethylglycyloxymethyl)theophylline.

10. The method of claim 1, wherein said compound is: 7-Ethoxymethyl-theophylline.

11. The method of claim 1, wherein said compound is: 7-Butyloxymethyl-theophylline.

12. The method of claim 1, wherein said compound is: 7-Benzyloxymethyl-theophylline.

13. The method of claim 1, wherein said compound is: 7-(1-Pyridyl)methyl-theophylline chloride.

14. The method of claim 1, wherein said compound is: 7-(N,N-dimethylaminoethyoxyl)methyl-theophylline.

15. The method of claim 1, wherein said compound is: 7-Acetyloxymethyl-theophylline.

16. The method of claim 1, wherein said compound is: 7-Butanoyloxymethyl-theophylline.

17. The method of claim 1, wherein said compound is: 7-Ethoxycarbonyloxymethyl-theophylline.

18. The method of claim 1, wherein said compound is: 7-Benzyloxycarbonyloxymethyl-theophylline.

19. The method of claim 1, wherein said compound is: 7-(2′, 2′, 2′,-Trichloroethyloxycarbonyloxymethyl)-theophylline.

20. The method of claim 1, wherein said compound is: 7-(N,N-Dimethylglycyloxymethyl)-theophylline.

21. The method of claim 1, wherein said compound is: 7-(1-Piperidylacetyloxymethyl)-theophylline.

22. The method of claim 1, wherein said compound is: 7-p-Toluyloxymethyl-theophylline.

23. The method of claim 1, wherein said compound is: 7-Phenylacetyloxymethyl-theophylline.

24. The method of claim 1, wherein said compound is: 7-Picolinoyloxymethyl-theophylline.

25. The method of claim 1, wherein said compound is: 7-N-Formylglycyloxymethyl-theophylline.

26. The method of claim 1, wherein said compound is: 7-Glycyloxymethyl-theophylline.

27. The method of claim 1, wherein said compound is: 7-Cinnamoyloxymethyl-theophylline.

28. The method of claim 1, wherein said compound is: 7-Methylsuccinyloxymethyl-theophylline.

29. The method of claim 1, wherein said compound is: 7-(N,N-Dimethylsuccinamyloxymethyl)-theophylline.

30. The method of claim 1, wherein said compound is: 7-(N,N,N-Trimethylglycyloxymethyl)-theophylline chloride.

31. The method of claim 1, wherein said compound is: 7-($\alpha$-Ethoxyethyl)-theophylline.

32. The method of claim 1, wherein said compound is: 7-($\alpha$-Benzyloxyethyl)-theophylline.

33. The method of claim 1, wherein said compound is: 7-($\alpha$-Acetyloxyethyl)-theophylline.

34. The method of claim 1, wherein said compound is: 7-($\alpha$-Butanoyloxyethyl)-theophylline.

35. The method of claim 1, wherein said compound is: 7-($\alpha$-Pivalyloxyethyl)-theophylline.

36. The method of claim 1, wherein said compound is: 7-($\alpha$-Ethoxycarbonyloxyethyl)-theophylline.

37. The method of claim 1, wherein said compound is: 7-[$\alpha$-(N,N-Dimethylglycyloxy)ethyl]-theophylline.

38. The method of claim 1, wherein said compound is: 7-($\alpha$-Benzoyloxyethyl)-theophylline.

39. The method of claim 1, wherein said compound is: 7-[$\alpha$-(N,N-Dimethylsuccinamyloxy)ethyl]-theophylline.

40. The method of claim 1, wherein said compound is: 7-[$\alpha$-(N,N,N-Trimethylglycyloxy)ethyl]-theophylline chloride.

41. The method of claim 1, wherein said compound is: 7-($\alpha$-Benzyloxybenzyl)-theophylline.

42. The method of claim 1, wherein said compound is: 7-($\alpha$-Acetyloxybenzyl)-theophylline.

43. The method of claim 1, wherein said compound is: 7-($\alpha$-Butanoyloxybenzyl)-theophylline.

44. The method of claim 1, wherein said compound is: 7-($\alpha$-Ethoxycarbonyloxybenzyl)-theophylline.

45. The method of claim 1, wherein said compound is: 7-[$\alpha$-(N,N-Dimethylglycyloxy)benzyl]-theophylline.

46. The method of claim 1, wherein said compound is: 7-[$\alpha$-(N-Formylglycyloxy)benzyl]-theophylline.

47. The method of claim 1, wherein said compound is: 7-($\alpha$-Methylsuccinyloxybenzyl)-theophylline.

48. The method of claim 1, wherein said compound is: 7-[$\alpha$-(N,N,-Dimethylsuccinamyloxy)benzyl]-theophylline.

49. The method of claim 1, wherein said compound is: 7-[$\alpha$-(N,N,N-Trimethylglycyloxy)benzyl]-theophylline chloride.

50. The method of claim 1, wherein said compound is: 7-Ethoxymethyl-1-methyl-3-isobutylxanthine.

51. The method of claim 1, wherein said compound is: 7-Butyloxymethyl-1-methyl-3-isobutylxanthine.

52. The method of claim 1, wherein said compound is: 7-Benzyloxymethyl-1-methyl-3-isobutylxanthine.

53. The method of claim 1, wherein said compound is: 7-(1-Pyridyl)methyl-1-methyl-3-isobutylxanthine chloride.

54. The method of claim 1, wherein said compound is: 7-(N,N-dimethylaminoethyloxy)methyl-1-methyl-3-isobutylxanthine.

55. The method of claim 1, wherein said compound is: 7-Acetyloxymethyl-1-methyl-3-isobutylxanthine.

56. The method of claim 1, wherein said compound is: 7-Butanoyloxymethyl-1-methyl-3-isobutylxanthine.

57. The method of claim 1, wherein said compound is: 7-Pivalyloxymethyl-1-methyl-3-isobutylxanthine.

58. The method of claim 1, wherein said compound is: 7-Hexanoyloxymethyl-1-methyl-3-isobutylxanthine.

59. The method of claim 1, wherein said compound is: 7-Ethoxycarbonyloxymethyl-1-methyl--3-isobutylxanthine.

60. The method of claim 1, wherein said compound is: 7-Benzyloxycarbonyloxymethyl-1-methyl-3-isobutylxanthine.

61. The method of claim 1, wherein said compound is: 7-(2', 2', 2'-Trichloroethyloxycarbonyloxymethyl)-1-methyl-3-isobutylxanthine.

62. The method of claim 1, wherein said compound is: 7-(N,N,-Dimethylglycyloxymethyl)-1-methyl-3-isobutylxanthine.

63. The method of claim 1, wherein said compound is: 7-(1-Piperidylacetyloxymethyl)-1-methyl-3-isobutylxanthine.

64. The method of claim 1, wherein said compound is: 7-p-Toluyloxymethyl-1-methyl-3-isobutylxanthine.

65. The method of claim 1, wherein said compound is: 7-Phenylacetyloxymethyl-1-methyl-3-isobutylxanthine.

66. The method of claim 1, wherein said compound is: 7-Picolinoyloxymethyl-1-methyl-3-isobutylxanthine.

67. The method of claim 1, wherein said compound is: 7-N-Formylglycyloxymethyl-1-methyl-3-isobutylxanthine.

68. The method of claim 1, wherein said compound is: 7-Glycyloxymethyl-1-methyl-3-isobutylxanthine.

69. The method of claim 1, wherein said compound is: 7-Cinnamoyloxymethyl-1-methyl-3-isobutylxanthine.

70. The method of claim 1, wherein said compound is: 7-Methylsuccinyloxymethyl-1-methyl-3-isobutylxanthine.

71. The method of claim 1, wherein said compound is: 7-(N,N-Dimethylsuccinamyloxymethyl)-1-methyl-3-isobutylxanthine.

72. The method of claim 1, wherein said compound is: 7-(N,N,N-Trimethylglycyloxymethyl)-1-methyl-3-isobutylxanthine chloride.

73. The method of claim 1, wherein said compound is: 7-($\alpha$-Ethoxyethyl)-1-methyl-3-isobutylxanthine.

74. The method of claim 1, wherein said compound is: 7-($\alpha$-Benzyloxyethyl)-1-methyl-3-isobutylxanthine.

75. The method of claim 1, wherein said compound is: 7-($\alpha$-Acetyloxyethyl)-1-methyl-3-isobutylxanthine.

76. The method of claim 1, wherein said compound is: 7-($\alpha$-Butanoyloxyethyl)-1-methyl-3-isobutylxanthine.

77. The method of claim 1, wherein said compound is: 7-($\alpha$-Pivalyloxyethyl)-1-methyl-3-isobutylxanthine.

78. The method of claim 1, wherein said compound is: 7-($\alpha$-Ethoxycarbonyloxyethyl)-1-methyl-3-isobutylxanthine.

79. The method of claim 1, wherein said compound is: 7-[$\alpha$-(N,N-Dimethylglycyloxy)ethyl]-1-methyl-3-isobutylxanthine.

80. The method of claim 1, wherein said compound is: 7-($\alpha$-Benzoyloxyethyl)-1-methyl-3-isobutylxanthine.

81. The method of claim 1, wherein said compound is: 7-[$\alpha$-(N,N-Dimethylsuccinamyloxy)ethyl-1-methyl-3-isobutylxanthine.

82. The method of claim 1, wherein said compound is: 7-[$\alpha$-(N,N,N-Trimethylglycyloxy)ethyl]-1-methyl-3-isobutylxanthine chloride.

83. The method of claim 1, wherein said compound is: 7-($\alpha$-Benzyloxybenzyl)-1-methyl-3-isobutylxanthine.

84. The method of claim 1, wherein said compound is: 7-($\alpha$-Acetyloxybenzyl)-1-methyl-3-isobutylxanthine.

85. The method of claim 1, wherein said compound is: 7-($\alpha$-Butanoyloxybenzyl)-1-methyl-3-isobutylxanthine.

86. The method of claim 1, wherein said compound is: 7-($\alpha$-Ethoxycarbonyloxybenzyl)-1-methyl-3-isobutylxanthine.

87. The method of claim 1, wherein said compound is: 7-[$\alpha$-(N,N-Dimethylglycyloxy)benzyl]-1-methyl-3-isobutylxanthine.

88. The method of claim 1, wherein said compound is: 7-[$\alpha$-(N-Formylglycyloxy)benzyl]-1-methyl-3-isobutylxanthine.

89. The method of claim 1, wherein said compound is: 7-($\alpha$-Methylsuccinyloxybenzyl)-1-methyl-3-isobutylxanthine.

90. The method of claim 1, wherein said compound is: 7-[$\alpha$-(N,N-Dimethylsuccinamyloxy)benzyl]-1-methyl-3-isobutylxanthine.

91. The method of claim 1, wherein said compound is: 7-[$\alpha$-(N,N,N-Trimethylglycyloxy)benzyl]-1-methyl-3-isobutylxanthine chloride.

92. The method of claim 1, wherein said compound is: 7-Acetylthiomethyl-theophylline.

93. The method of claim 1, wherein said compound is: 7-Propionylthiomethyl-theophylline.

94. The method of claim 1, wherein said compound is: 7-(N,N-Dimethylglycylthiomethyl)-theophylline.

95. The method of claim 1, wherein said compound is: 7-p-Toluylthiomethyl-theophylline.

96. The method of claim 1, wherein said compound is: 7-Cinnamoylthiomethyl-theophylline.

97. The method of claim 1, wherein said compound is: 7-(N,N-Diethylsuccinamylthiomethyl)-theophylline.

98. The method of claim 1, wherein said compound is combined with a pharmaceutically acceptable topical carrier material.

99. The method of claim 98, wherein said pharmaceutically acceptable topical carrier material is triacetin.

* * * * *